United States Patent [19]

St. Ville

[11] Patent Number: 5,594,651
[45] Date of Patent: Jan. 14, 1997

[54] METHOD AND APPARATUS FOR MANUFACTURING OBJECTS HAVING OPTIMIZED RESPONSE CHARACTERISTICS

[76] Inventor: James A. St. Ville, 2500 N. 24th St., Suite 200, Phoenix, Ariz. 85008

[21] Appl. No.: 388,580

[22] Filed: Feb. 14, 1995

[51] Int. Cl.$^6$ .............................. G06F 19/00; G06F 17/50
[52] U.S. Cl. ................ 364/468.04; 364/468.13; 364/512
[58] Field of Search .................... 364/468, 401–403, 364/474.24, 512, 191, 474.05, 508, 468.03, 468.04, 468.24, 468.25, 468.13, 148, 474.15; 395/118, 119, 120, 161

[56] References Cited

U.S. PATENT DOCUMENTS

| | | | |
|---|---|---|---|
| 4,909,127 | 3/1990 | Skelton et al. | 87/33 |
| 4,936,862 | 6/1990 | Walker et al. | 364/468 X |
| 4,975,262 | 12/1990 | Suto et al. | 423/447.1 |
| 5,023,800 | 6/1991 | Carver et al. | 364/474.24 |
| 5,351,196 | 9/1994 | Sowar et al. | 364/468 X |
| 5,487,012 | 1/1996 | Topholm et al. | 364/468 X |

OTHER PUBLICATIONS

James A. St. Ville et al., "The Anatomy of Midthigh Pain After Total Hip Arthroplasty", Johns Hopkins APL Technical Digest, Apr.–Jun. 1991, vol. 12, No. 2, pp. 198–212.

*Primary Examiner*—Joseph Ruggiero
*Attorney, Agent, or Firm*—Banner & Witcoff, Ltd.

[57] ABSTRACT

A method for manufacturing an object having a potential $\{x\}$ which is generated in response to a field $\{f\}$ applied thereto is provided. The method includes the step of designing a geometric model of the object. A computerized mathematical model of the object is generated by discretizing the geometric model of the object into a plurality of finite elements and defining nodes at boundaries of the elements, wherein values of the field $\{f\}$ and potential $\{x\}$ are specified at the nodes. A material property matrix $[k]$ is then calculated based on the relationship $\{f\}=[k]\{x\}$. Material property coefficients are then extracted from the material property matrix $[k]$ for each finite element in the computerized mathematical model and the extracted material property coefficients are compared to material property coefficients for known materials to match the extracted material property coefficients to the material property coefficients for known materials. Manufacturing parameters corresponding to the matched material property coefficients are then determined. The object is then manufactured in accordance with the determined manufacturing parameters.

24 Claims, 11 Drawing Sheets m = NODE NUMBER
(m) = ELEMENT NUMBER
$K^{(m)}$ = SPRING STIFFNESS OF ELEMENT (m)

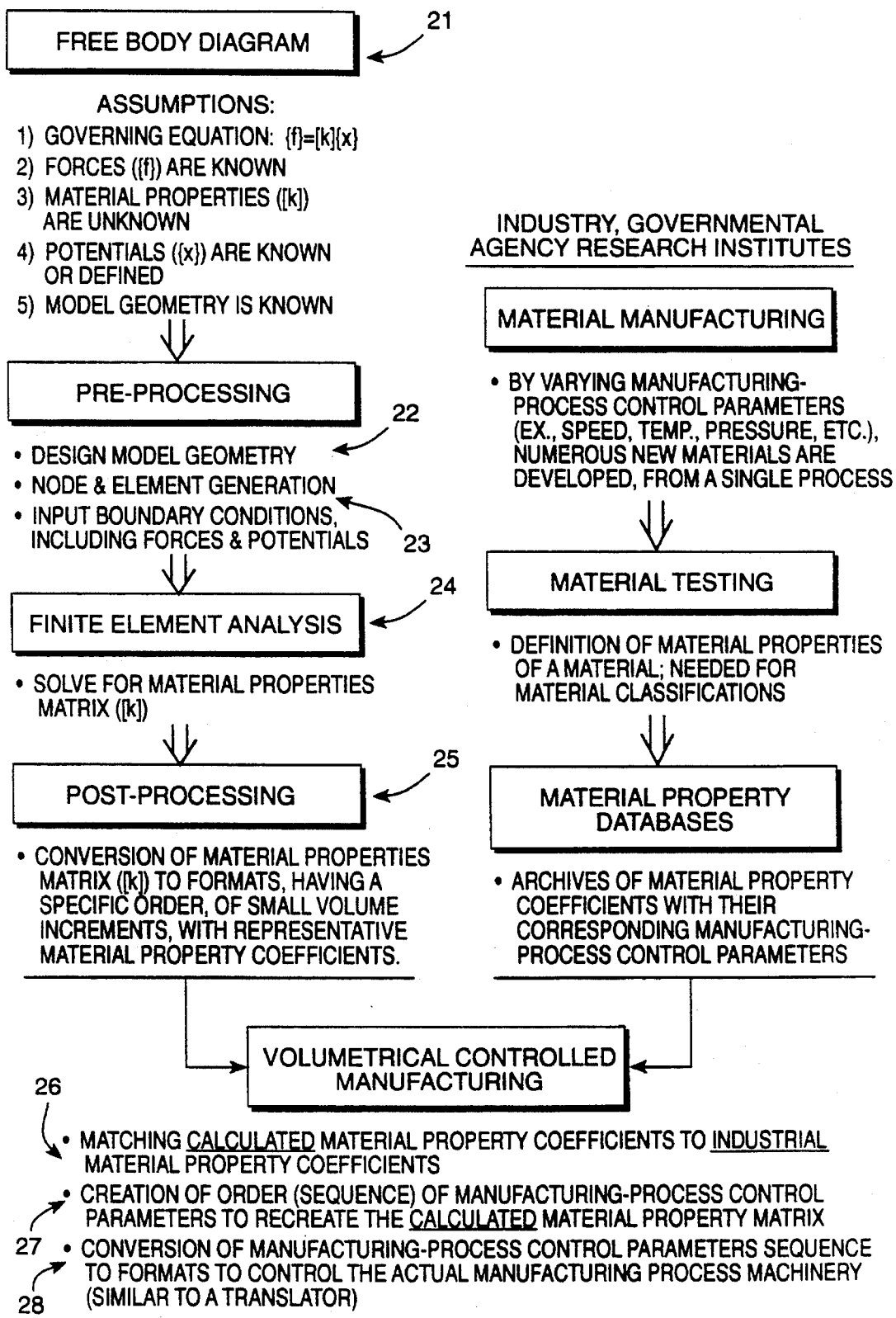

| | INTACT FEMUR |
|---|---|
| A | 0.221 ± 0.057 |
| B | 0.875 ± 0.119 |
| C | 0.698 ± 0.122 |
| D | 1.217 ± 0.150 |
| E | 1.315 ± 0.131 |
| F | 1.208 ± 0.131 |

| M1-1 | E1-1 | σ1-1 | PROCESS | PROCESS PARAMETERS |
|---|---|---|---|---|
| M1-2 | E1-2 | σ1-2 | PROCESS | PROCESS PARAMETERS |
| ⋮ | ⋮ | ⋮ | ⋮ | ⋮ |
| M1-n | E1-n | σ1-n | PROCESS | PROCESS PARAMETERS |

| M2-1 | σ'2-1 | PROCESS | PROCESS PARAMETERS |
|---|---|---|---|
| M2-2 | σ'2-2 | PROCESS | PROCESS PARAMETERS |
| ⋮ | ⋮ | ⋮ | ⋮ |
| M2-n | σ'2-n | PROCESS | PROCESS PARAMETERS |

METHOD AND APPARATUS FOR MANUFACTURING OBJECTS HAVING OPTIMIZED RESPONSE CHARACTERISTICS

BACKGROUND OF THE INVENTION

1. Technical Field

The present invention generally relates to articles of manufacture and, more particularly, to a method and apparatus for manufacturing objects having response characteristics which are optimized for a desired application or use.

2. Description of Related Art

An object composed of one or more materials, which is engineered and manufactured for an intended application, must be able to withstand the stresses exerted on the object during use in the application. For example, a bridge, carrying a pathway or roadway over a depression or obstacle such as a body of water, must be designed to withstand the stresses created by traffic (either pedestrian or vehicle or both), temperature variations, wind, shifts in the surface of the earth which may be caused by earthquakes or other geological movements, etc. Similarly, aircraft components must have sufficient strength to withstand bending, sheer, torsion, and other forces placed on it. Accordingly, in a conventional engineering process, a stress analysis is performed. The stress analysis requires a determination of the forces (or "stress-field") which will be applied to the object during use in the application. These stresses include, for example, thermal, mechanical, and electromagnetic forces. Knowing the stress-field enables a determination of whether a trial design and the selected material(s) are appropriate to withstand the stresses created during use of the object for its intended application. If a specific combination of design and material(s) is not suitable for an intended application, the object may be redesigned and/or new material(s) may be selected.

The above-described conventional engineering process will be discussed in greater detail with respect to FIG. 1. The initial design geometry of the object and the material(s) of which the object is to be composed are defined at step 11. Geometry includes dimensions, tolerances, surface finish, definitions of surfaces and edges, and, in some cases, the fit between two mating parts. The initial design geometry may be created using computer-aided-design (CAD) techniques known in the art. Each force which will be applied to the object during intended use, and the points and direction of application of the respective forces, are identified at step 12.

Stress analysis is performed at step 13. One technique for carrying out such a stress analysis is to create a finite-element model of the object and utilize the finite element method to determine the suitability of the object for the intended application. The finite element method is a numerical analysis technique for obtaining approximate solutions to a wide variety of engineering problems in which a complex part or object is subdivided into the analyses of small simple subdivisions of the part or object. This method has been widely discussed and reference will be made in what follows to a discussion from Huebner et al, *The Finite Element Method for Engineers*, Third Edition, John Wiley and Sons, Inc. (1995). In a continuum problem, a field variable such as pressure, temperature, displacement, or stress has infinitely many values because it is a function of each point in the body. The finite element method reduces the problem to one of a finite number of unknowns by dividing the solution region into elements and by expressing the unknown field variable in terms of assumed approximating functions within each element. The approximating functions are defined in terms of the values of the field variables at specified points called nodes. Nodes usually lie on the element boundaries where adjacent elements are connected. For the finite element representation of a problem, the nodal values of the field variable become the unknowns. Once these unknowns are found, the approximating functions define the field variable throughout the assembled elements. An important feature of the finite element method is the ability to formulate solutions for individual elements before putting them together to represent the entire problem. This means that the characteristics of each individual element may be found and then the elements may be assembled to find the characteristics of the whole structure. The finite element method may be summarized by the following steps.

First, the continuum is discretized into elements. A variety of element shapes may be used and different element shapes may be employed in the same solution region. The number and type of elements in a given problem are generally matters of engineering judgment. For example, three-dimensional elements work best if they are either tetrahedral or hexahedral in shape. In addition, the most accurate elements have a unity aspect ratio, The next step is to assign nodes to each element and then choose the interpolation function to represent the variation of the field variable over the element. Once the finite element model has been established, the matrix equations expressing the properties of the individual elements may be determined. Several different approaches including a direct approach, a variational approach, or a weighted residual approach may be used. The element properties are then assembled to obtain the system equations. That is, the matrix equations expressing the behavior of the elements are combined to form the matrix equations expressing the behavior of the entire system. At this point, the system equations are modified to account for any boundary conditions of the problem. That is, known nodal values of the dependent variables or nodal loads are imposed. The resulting system of equations may then be solved to obtain the unknown nodal values of the problem. The solution of equations may be used to calculate other important parameters. For example, in a structural problem, the nodal unknowns are displacement components. From these displacements, the element strains and stresses may be calculated.

An example of the finite element method from the Huebner text will be discussed as an aid in understanding the terminology to be used in this specification. FIG. 2 illustrates a linear spring system. For a typical spring element, the relations expressing its stiffness are $$\begin{bmatrix} k_{11} & -k_{12} \\ -k_{21} & k_{22} \end{bmatrix} \begin{Bmatrix} \delta_1 \\ \delta_2 \end{Bmatrix} = \begin{Bmatrix} F_1 \\ F_2 \end{Bmatrix}$$

where $k_{11}=k_{12}=k_{21}=k_{22}=k$.

Under a given loading condition, each element as well as the system of elements, must be in equilibrium. If this equilibrium condition is imposed at a particular node i, $$\Sigma F_i^{(e)} = F_i^{(1)} + F_i^{(2)} + F_i^{(3)} + \ldots = R_i \tag{1}$$

which states that the sum of all the nodal forces in one direction at node i equals the resultant external load applied at node i. In accordance with conventional tensor notation, each coefficient in a stiffness matrix is assigned a double subscript, e.g., ij; the number i is the subscript designating the force $F_i$ produced by a unit value of the displacement whose subscript is j. The force $F_i$ is that which exists when $\delta_j=1$ and all the other displacements are fixed. A displacement and a resultant force in the direction of the displacement carry the same subscript. Thus, evaluating equation (1) at each node in the linear spring system of FIG. 2, it can be shown that at node 1, $$k_{11}^{(1)}\delta_1 + k_{12}^{(1)}\delta_2 = R_1$$

at node 2, $$k_{21}^{(1)}\delta_1 + (k_{22}^{(1)} + k_{22}^{(2)} + k_{22}^{(3)})\delta_2 + (k_{23}^{(2)} + k_{23}^{(3)})\delta_3 = 0$$

at node 3, $$(k_{32}^{(2)} + k_{32}^{(3)})\delta_2 + (k_{33}^{(2)} + k_{33}^{(3)} + k_{33}^{(4)})\delta_3 + k_{34}^{(4)}\delta_4 = 0$$

and at node 4

$$k_{43}^{(4)}\delta_3 + k_{44}^{(4)}\delta_4 = F$$

Using matrix notation, these system equilibrium equations can be written as $$\begin{bmatrix} k_{11}^{(1)} & k_{12}^{(1)} & 0 & 0 \\ k_{21}^{(1)} & (k_{22}^{(1)} + k_{22}^{(2)} + k_{22}^{(3)}) & (k_{23}^{(2)} + k_{23}^{(3)}) & 0 \\ 0 & (k_{32}^{(2)} + k_{32}^{(3)}) & (k_{33}^{(2)} + k_{33}^{(3)} + k_{33}^{(4)}) & k_{34}^{(4)} \\ 0 & 0 & k_{43}^{(4)} & k_{44}^{(4)} \end{bmatrix} \begin{Bmatrix} \delta_1 \\ \delta_2 \\ \delta_3 \\ \delta_4 \end{Bmatrix} = \begin{Bmatrix} R_1 \\ 0 \\ 0 \\ F \end{Bmatrix}$$

or $$[k]\{\delta\} = \{F\} \quad (2)$$

These equations are the assembled force-displacement characteristics for the complete system and [k] is the assembled stiffness matrix. These equations cannot be solved for the nodal displacements until they have been modified to account for the boundary conditions.

It can be seen that the stiffness matrix [k] is the sum of the following matrices, each matrix representing the contribution from a corresponding one of the elements:

$$[\overline{K}]^{(1)} = \begin{bmatrix} k_{11}^{(1)} & k_{12}^{(1)} & 0 & 0 \\ k_{21}^{(1)} & k_{22}^{(1)} & 0 & 0 \\ 0 & 0 & 0 & 0 \\ 0 & 0 & 0 & 0 \end{bmatrix} \quad [\overline{K}]^{(2)} = \begin{bmatrix} 0 & 0 & 0 & 0 \\ 0 & k_{22}^{(2)} & k_{23}^{(2)} & 0 \\ 0 & k_{32}^{(2)} & k_{33}^{(2)} & 0 \\ 0 & 0 & 0 & 0 \end{bmatrix}$$

$$[\overline{K}]^{(3)} = \begin{bmatrix} 0 & 0 & 0 & 0 \\ 0 & k_{22}^{(3)} & k_{23}^{(3)} & 0 \\ 0 & k_{32}^{(3)} & k_{33}^{(3)} & 0 \\ 0 & 0 & 0 & 0 \end{bmatrix} \quad [\overline{K}]^{(4)} = \begin{bmatrix} 0 & 0 & 0 & 0 \\ 0 & 0 & 0 & 0 \\ 0 & 0 & k_{33}^{(4)} & k_{34}^{(4)} \\ 0 & 0 & k_{43}^{(4)} & k_{44}^{(4)} \end{bmatrix}$$

Thus, it can be seen that the assembled or global stiffness matrix can be obtained simply by adding the contribution of each element. Similarly, using boolean locating functions or other locating functions, the contribution of each element may be determined from the assembled or global stiffness matrix.

Thus, to perform stress analysis, the material(s) of which the object is composed as determined by the initial design, the forces which are applied to the object as identified at step 12, and any constraints or boundary conditions are input into the finite element model. Since the forces {f} and the material property matrix [k] are known, the finite element method is used to determine the corresponding displacements {δ} using equation (2). For example, assume the forces determined at step 12 are loads applied to the object. Then, since the material property matrix is determined by the initial choice of material(s), the displacement resulting from application of the loads may be determined. As noted above, these displacements may then be used to calculate the stresses and strains. The calculations for solving the matrix equations generated by the finite element method are generally performed using a suitable finite element software package.

Post-processing, indicated at step 14, is carried out to determine if the design will perform satisfactorily. Such post-processing may include, for example, a comparison of the stresses in the material to the maximum allowable stresses dictated by the material used. If the stresses are too high, the process returns to step 11 where the part may be made stronger by adding material, the material may be changed to one with higher allowable stress, or a new design geometry may be utilized. If the post-processing at step 14 indicates the results are acceptable, the process proceeds to step 15 where the object is manufactured in accordance with the design geometry and the choice of material(s) determined at step 11.

A known problem with the conventional manufacturing technique described above is that it uses known materials and pre-set manufacturing parameters, thereby creating a structure with fixed intrinsic (constitutive) properties. This results in over designing and inefficiency of the structure. While manufacturing processes exist that enable the adjustment of manufacturing parameters, no method exists of precisely determining what the manufacturing parameters should be or the sequence in which they should be implemented so as to optimize the constitutive properties of a particular object design. In essence, no method exists for determining an optimized constitutive matrix for a particular object or for manufacturing the object in accordance with this optimized constitutive matrix.

SUMMARY OF THE INVENTION

In accordance with the present invention, a method for manufacturing an object having a potential {x} which is generated in response to a field {f} applied thereto includes the step of designing a geometric model of the object. A computerized mathematical model of the object is generated by discretizing the geometric model of the object into a plurality of finite elements and defining nodes at boundaries of the elements, wherein values of the field {f} and potential {x} are specified at the nodes. A material property matrix [k] is then calculated based on the relationship {f}=[k]{x}. Material property coefficients are then extracted from the material property matrix [k] for each finite element in the computerized mathematical model and the extracted material property coefficients are compared to material property coefficients for known materials to match the extracted material property coefficients to the material property coefficients for known materials. Manufacturing parameters corresponding to the matched material property coefficients are then determined. The object is then manufactured in accordance with the determined manufacturing parameters.

In accordance with another aspect of the present invention, a method for determining manufacturing parameters for manufacturing an object having a potential {x} which is generated in response to a field {f} applied thereto includes the step of designing a geometric model of the object. A computerized mathematical model of the object is generated by discretizing the geometric model of the object into a plurality of finite elements and defining nodes at boundaries of the elements, wherein values of the field {f} and potential {x} are specified at the nodes. A material property matrix [k] is calculated based on the relationship {f}=[k]{x}. Material property coefficients are extracted from the material property matrix [k] for each finite element in the computerized mathematical model and the extracted material property coefficients are compared to material property coefficients for known materials to match the extracted material property coefficients to the material property coefficients for known materials. Manufacturing parameters corresponding to the matched material property coefficients are then determined.

In accordance with yet another aspect of the present invention, a method for determining the material properties of an object having a potential {x} which is generated in response to a field {f} applied thereto includes the step of designing a geometric model of the object. A computerized mathematical model of the object is generated by discretizing the geometric model of the object into a plurality of finite elements and defining nodes at boundaries of the elements, wherein values of the field {f} and potential {x} are specified at the nodes. A material property matrix [k] is calculated based the relationship {f}=[k]{x}. Material property coefficients are extracted from the material property matrix [k] for each finite element in the computerized mathematical model and the extracted material property coefficients are compared to material property coefficients for known materials to match the extracted material property coefficients to the material property coefficients for known materials.

In accordance with yet another aspect of the present invention, a machine for determining the manufacturing parameters of an object having a potential {x} which is generated in response to a field {f} applied thereto includes a designing element for designing a geometric model of the object. A generating element generates a computerized mathematical model of the object by discretizing the geometric model of the object into a plurality of finite elements and defining nodes at boundaries of the elements, wherein values of the field {f} and the potential {x} are specified at the nodes. A calculating element calculates a material property matrix [k] based the relationship {f}=[k]{x}. An extracting element extracts material property coefficients from the material property matrix [k] for each finite element in the computerized mathematical model. A comparing element compares the extracted material property coefficients to material property coefficients for known materials to match the extracted material property coefficients to the material property coefficients for known materials and a determining means determines manufacturing parameters corresponding to the matched material property coefficients.

In accordance with yet another aspect of the present invention, a machine for determining the material properties of an object having a potential {x} which is generated in response to a field {f} applied thereto includes a designing element for designing a geometric model of the object. A generating element generates a computerized mathematical model of the object by discretizing the geometric model of the object into a plurality of finite elements and defining nodes at boundaries of the elements, wherein values of the field {f} and the potential {x} are specified at the nodes. A calculating element calculates a material property matrix [k] based the relationship {f}=[k]{x}. An extracting element extracts material property coefficients from the material property matrix [k] for each finite element in the computerized mathematical model. A comparing element compares the extracted material property coefficients to material property coefficients for known materials to match the extracted material property coefficients to the material property coefficients for known materials.

These and other features and advantages of the present invention will be better understood from a reading of the following detailed description in conjunction with the accompanying drawings.

BRIEF DESCRIPTION OF THE DRAWINGS

FIG. 3 illustrates the methodology for manufacturing an object in accordance with the present invention.

DETAILED DESCRIPTION

Figure 1:
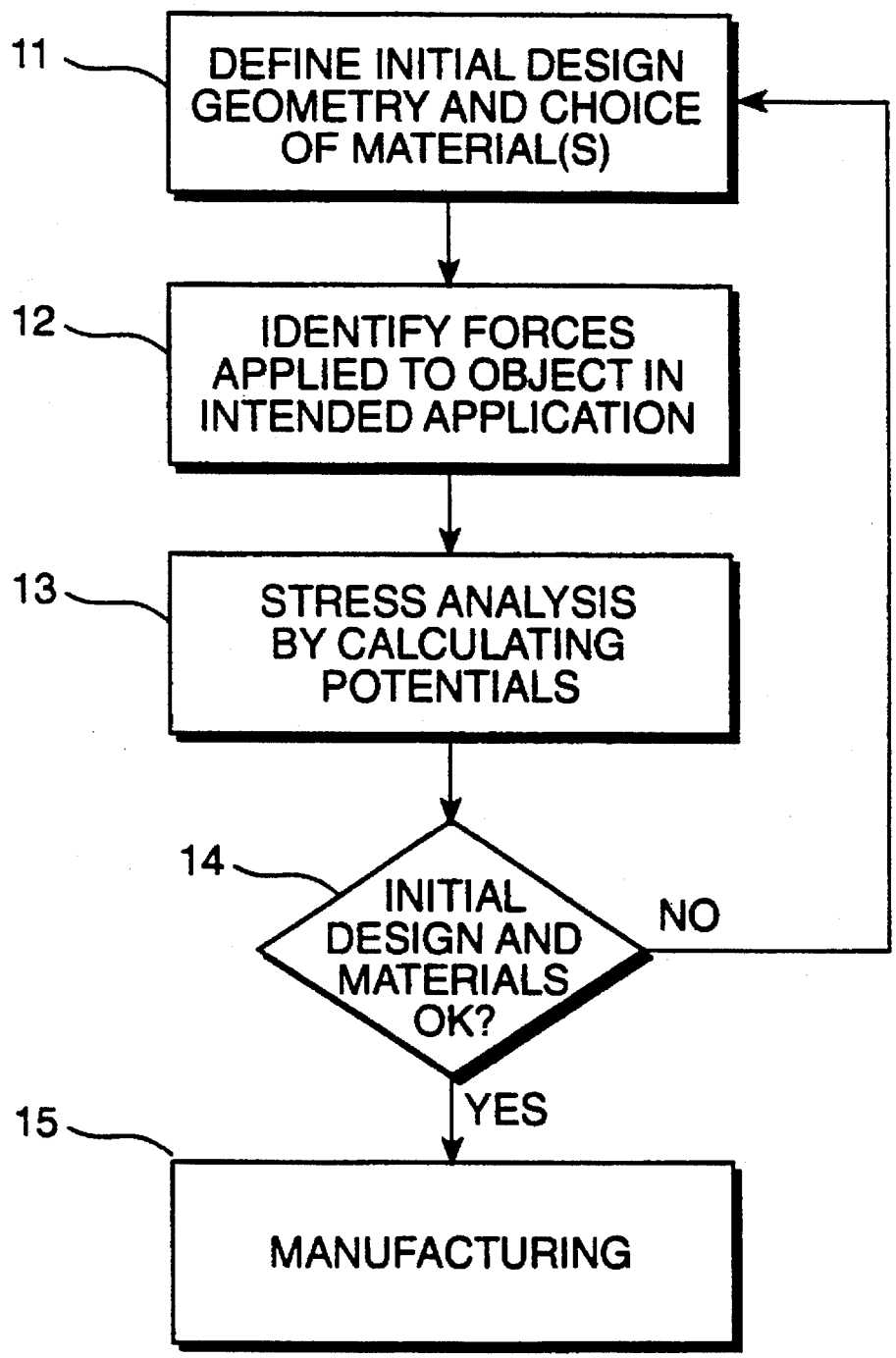
FIG. 1 illustrates the prior art methodology for manufacturing an object.
Figure 2:
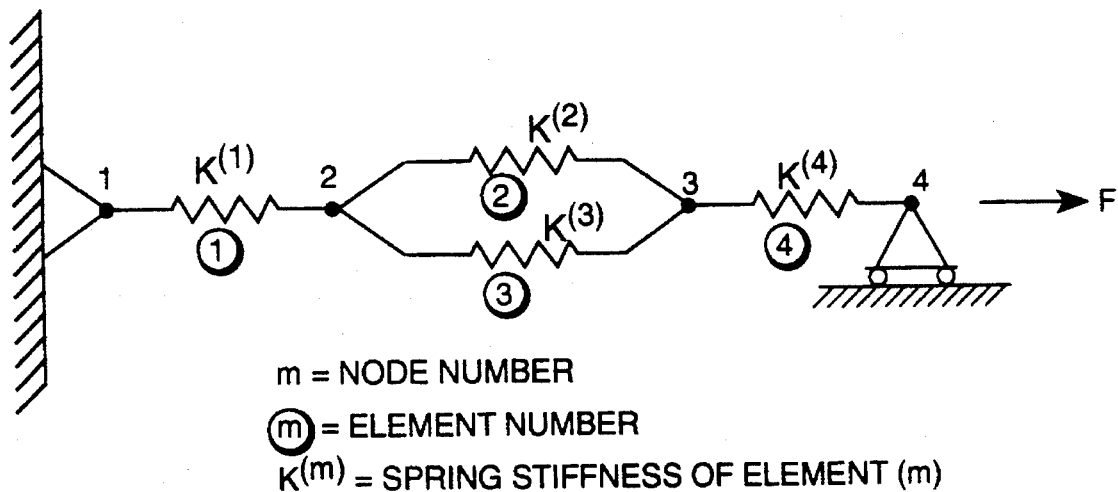
FIG. 2 illustrates a simple mechanical spring system for defining terminology used in this application.

FIG. 3 will be used to describe a methodology for manufacturing an object or part in accordance with the present invention. As will become apparent from the description below, object or part (hereinafter "object") as used herein refers to any object which may be manufactured by a process or technique in which manufacturing parameters may be controlled to vary constitutive or material properties within the object. The methodology for manufacturing an object in accordance with the instant invention is based on solutions of the equation $$\{f\}=[k]\{x\}$$

where {f} represents a field which will be applied to the object in its intended use, {x} represents a potential corresponding to the applied field, and [k] represents the material properties of the object.

The methodology of the instant invention may be utilized with any manufacturing technique in which the manufacturing parameters may be varied. For example, a braiding process using a braider may be used to manufacture fiber composite objects. Fiber composite materials are finding increasing use as the construction material for components such as body panels of automobiles, aircraft, prosthetic implants, golf club shafts, tennis rackets, bicycle frames, and fishing poles. These composite materials offer high strength equal to, or exceeding, that of metallic materials, for example, while at the same time are lighter in weight and have other improved functional properties. Parameters such as the speed of the braider bed and/or mandrel, the thickness of the fibers, and the tension applied to the fibers are controlled to vary the stiffness properties of the fiber composite material. An example of a braider bed designed for controlled braiding of composite materials is shown in U.S. Pat. No. 4,909,127 to Skelton. Three-dimension woven fabrics are also discussed in U.S. Pat. No. 4,975,262 to Suto.

Composite materials may also be constructed by laminating structural fibers in appropriate matrices compatible with these fibers as described in U.S. Pat. No. 5,023,800 to Carver et al. Fiberglass is a widely used composite system which incorporates glass fibers within an epoxy resin matrix. For formation of aircraft components, more exotic composite systems having improved properties are desirable. Currently available for use are exotic inorganic materials such as carbon fibers, boron fibers, improved glass fibers, aluminum oxide fibers, inorganic whiskers of different materials and certain organic fibers such as aramides and extended chain polyethylenes. These fibers or whiskers are incorporated as threads, fabrics, mats, or the like in appropriate resins, as for instance thermosetting epoxies, polyesters, polyethers, polyimides, and bismaleimides or thermoplastic polyamide-imines, polyether sulfones, polyether ketones, polyphenylene sulfides and other similar polymeric materials. Composite objects may be formed utilizing molding techniques—using either external molds which are of a complementary shape to an object or an internal mandrel type mold on which the composite object is built. A mold utilized for the formation and curing of a composite object is called a bonding tool and the curing is carried out under precisely controlled temperatures and pressures.

A contouring process using a contouring system on a lathe or a milling machine may be used to manufacture metal objects. Contouring refers to the continuous removal of material in an application such as turbine-blade machining. Parameters such as the part surface, the drive surface, and the check surface may be controlled to vary the milling tool path and thus the contouring. Part surface refers to the surface on which the end of the milling tool is riding; drive surface refers to the surface against which the edge of the milling tool rides; and check surface refers to a surface at which the current milling tool motion is to stop. Details of a contouring system are shown in Bedworth et al., *Computer-Integrated Design and Manufacturing*, McGraw-Hill Inc. (1991).

Of course, the instant invention is not limited to objects formed using braiding, molding, or contouring and the above discussions are merely examples of manufacturing techniques which may be utilized in the inventive methodology. Other processes and techniques include by way of example, but not by way of limitation, polymer manufacturing processes, crystallization techniques, ceramic manufacturing techniques, and the like.

At step 21, the field(s) $\{f\}$ which will be applied to the object in its intended use, as well as the desired potential(s) or response(s) $\{x\}$ to these field(s), are defined. For example, an object may be applied with a mechanical force field, an electric current field, a magnetic field, a thermal flux field, and/or a fluid velocity field. Other fields $\{f\}$ may be derived using these primary fields. For example, an acoustic field may be derived by combining the mechanical force field and the fluid velocity field. A magnetohydrodynamics field may be derived by combining the fluid velocity field and the magnetic field. Each of the above-identified fields has a corresponding potential. These potentials are displacement, corresponding to the mechanical force field; voltage, corresponding to the electric field; magnetic vector potential, corresponding to the magnetic field; temperature, corresponding to the thermal flux field; and fluid potential, corresponding to the fluid velocity field.

Figure 4A:
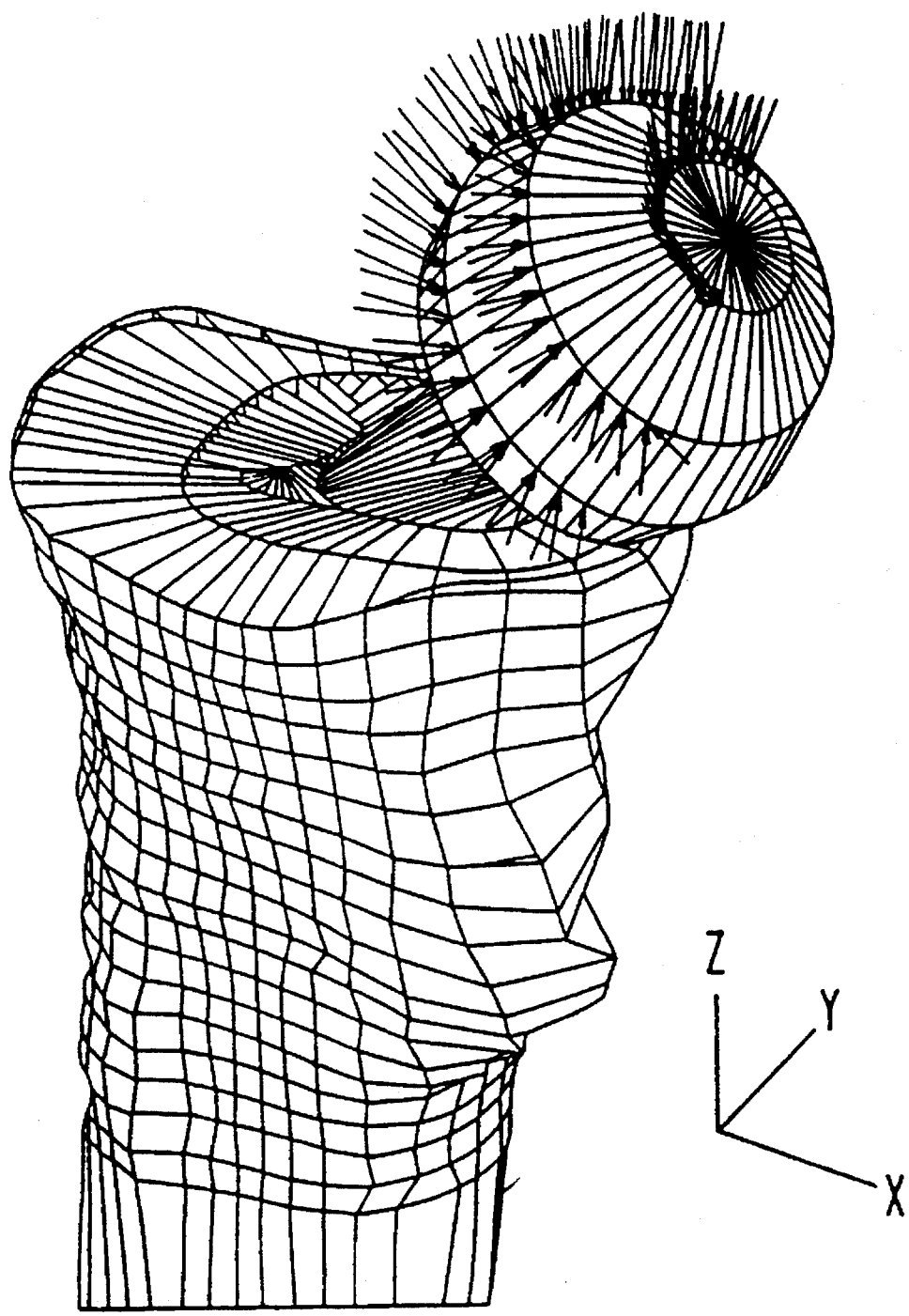
FIGS. 4A and 4B illustrate forces applied to the femoral head of a hip during a one-leg stance and rising from a chair, respectively.
Figure 4B:
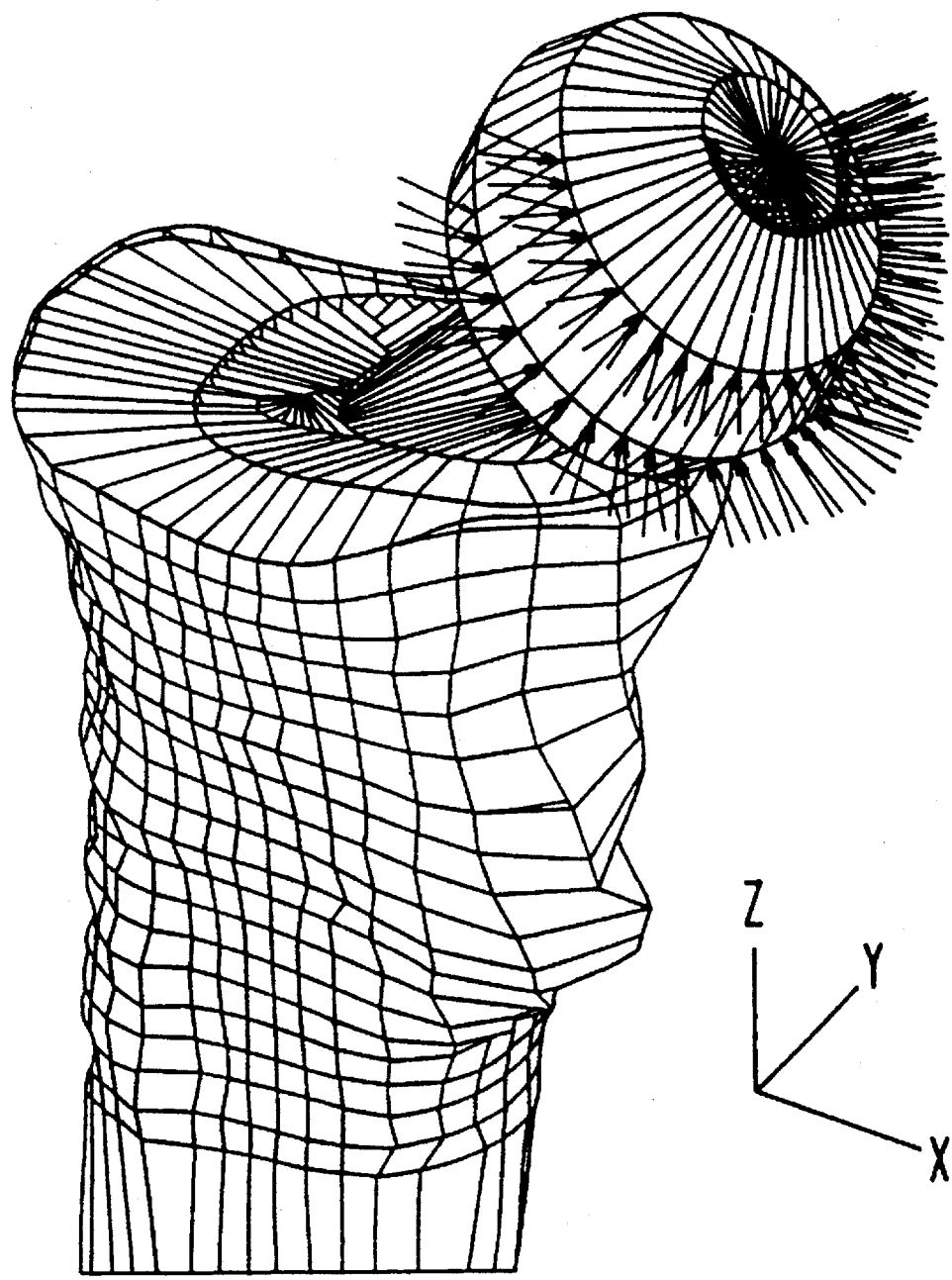

As noted, the fields defined at step 21 represent one or more fields which will be applied to the object in its intended use. For example, in the case of a prosthetic hip, the field may be the mechanical forces which will be applied to the prosthetic hip after implant in the human body. For example, the arrows in FIGS. 4A and 4B represent the forces (direction and magnitude) applied to the femoral head during a one-leg stance (during walking, for example) and rising from a chair, respectively. The force distributions and orientations are based on in vivo studies reported at, for example, Hodge et al., "Contact Pressures in the Human Hip Joint Measured In Vivo," *Proc. Natl. Acad. Sci. USA*, 83, 2879–2883 (1986). The resultant force of each of these forces was approximately 2000 Newtons (N), with an orientation change from one-leg stance to midrise loading. As another example, in the case of a heat conduction element, the field may be the thermal flux which will be applied to the object in its intended use. Of course, an object may be applied with more than one field and each of these fields may be defined at step 21. For example, an electrical conductor may be applied with an electric field, a magnetic field, and a mechanical force field in its intended use.

Figures 5A, 5B:
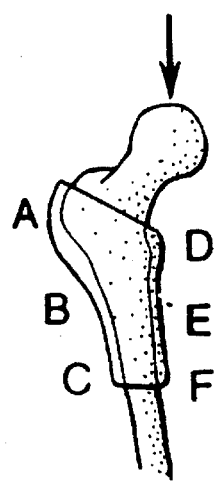
FIGS. 5A and 5B illustrate a force applied to an in vivo hip and the resultant stresses, respectively.

The potential(s) $\{x\}$ defined at step 21 define the manner in which the manufacturer desires the object to respond when the defined field or fields $\{f\}$ are applied thereto. In the case of the prosthetic hip, the defined potentials are the desired displacements (which correlate mathematically to the stresses) in the prosthetic hip when the prosthetic hip is subjected to the mechanical forces shown in FIGS. 4A and 4B during walking and rising from a chair. If the manufacturer desires the prosthetic hip to respond to forces in the same manner as an in vivo hip, the "desired displacements" in the prosthetic hip may, for example, correspond to the displacements generated in an in vivo hip during walking and rising from a chair. FIG. 5A illustrates an in vivo hip applied with a force of 2000N as indicated and FIG. 5B is a table setting forth measures of the displacements generated at the points labeled A, B, C, D, E, and F in FIG. 5A in response to this applied force. Thus, a manufacturer desiring to manufacture a prosthetic hip which responds to the force indicated in FIG. 5A in the same manner as an in vivo hip would define the force $\{f\}$ to be the force indicated in FIG. 5A and would define the displacements $\{x\}$ to be the displacements set forth in the table of FIG. 5B. Similarly, in the case of the heat conduction element which is applied with a thermal flux field, the defined responses correspond to desired temperatures at various portions of the heat conduction element when the defined thermal flux field is applied. In the case of an electrical conductor which is applied with an electric field, a magnetic field, and a mechanical force field, the defined responses correspond to desired displacements at various portions of the conductor when the defined mechanical force field is applied, to desired magnetic vector potentials at various portions of the conductor when the defined magnetic field is applied, and to desired voltages at various portions of the conductor when the defined electric field is applied, respectively.

At step 22, computer aided design is used to geometrically model the object to be manufactured. Geometric modeling is a technique of using computational geometry to define geometric objects. The purposes of geometric modeling are object representation, which mandates a complete definition of the object for manufacturing and other applications such as finite element analysis; design, which allows the user to input and manipulate a geometric specification of the object; and rendering, which uses the geometry to paint a realistic picture of the object on a computer graphics output device.

The initial geometric model of the object or part may, for example, be based on the experience of the design engineer or be dictated by the intended use of the object or part. For example, the initial geometric model of a prosthetic hip is based on an in vivo hip. Of course, this initial geometric model may be subsequently modified for adaptation to an individual of a particular height and/or weight. The initial design geometry of a golf club shaft is again known, i.e., a cylinder of predetermined length and diameter. Again, this initial design geometry may be modified to provide a shaft for a golfer of a particular height or to provide a shaft having a diameter which varies, e.g., a narrower diameter near the dub head. Suitable CAD software packages for carrying out this geometric modeling include I-DEAS (available from SDRC, Inc. of Milford, Ohio), CATIA (available from IBM of Armonk, N.Y.), and ANVIL-5000 (available from Manufacturing Consulting Services). These software packages may be run, for example, on UNIX-based work stations such as those available from Sun Microsystems or Silicon Graphics. Of course, the choice of computer will be determined by the computational power required and the invention is not limited in this respect. The use of such computer aided design software packages permits a geometric model of an object or part to be defined by a user and modified quickly and results in generation of geometry data which can be converted to formats useful in a computer aided manufacturing step and/or to formats useful a finite element method step, which steps are discussed in greater detail below. It is noted that the initial geometric modal can be image data generated by scanning an object having the desired geometry. For example, the initial geometric model in the case of a prosthetic hip can be generated by X-raying a cadaveric hip using, for example, a Siemens Somatom DR3 or a GE 9800 CT scanner. This image data may be converted to a format usable by the CAD software package or may be directly converted to a format usable by a finite element software package (for example., a PDA-PATRAN (available from PDA Engineering) format) to be described below.

At step 23, a finite dement modal of the object is generated using the finite dement method. The finite element method is based on the theory that an irregularly shaped object can be divided into smaller regular finite clements. Each element can then be treated separately and the aggregate effect is the sum of the effects of all of the finite elements in the object. The finite element modal is created by a user using an appropriate software package which operates on the geometric model developed in step 22. Thus, the finite element software package generally accesses a data file which contains the geometry of the object developed in step 21. Some integrated software packages, such as I-DEAS from SDRC, Inc., link modules for geometric modeling and finite element analysis so that the user does not have to redefine the geometry specifically for finite element analysis. Other suitable software packages for generating the finite element model include MSC/NASTRAN (available from MacNeal-Schwendler Corporation), ABAQUS (available from MacNeal-Schwendler Corporation), and ANSYS (available from Swanson Manufacturing).

Figure 6:
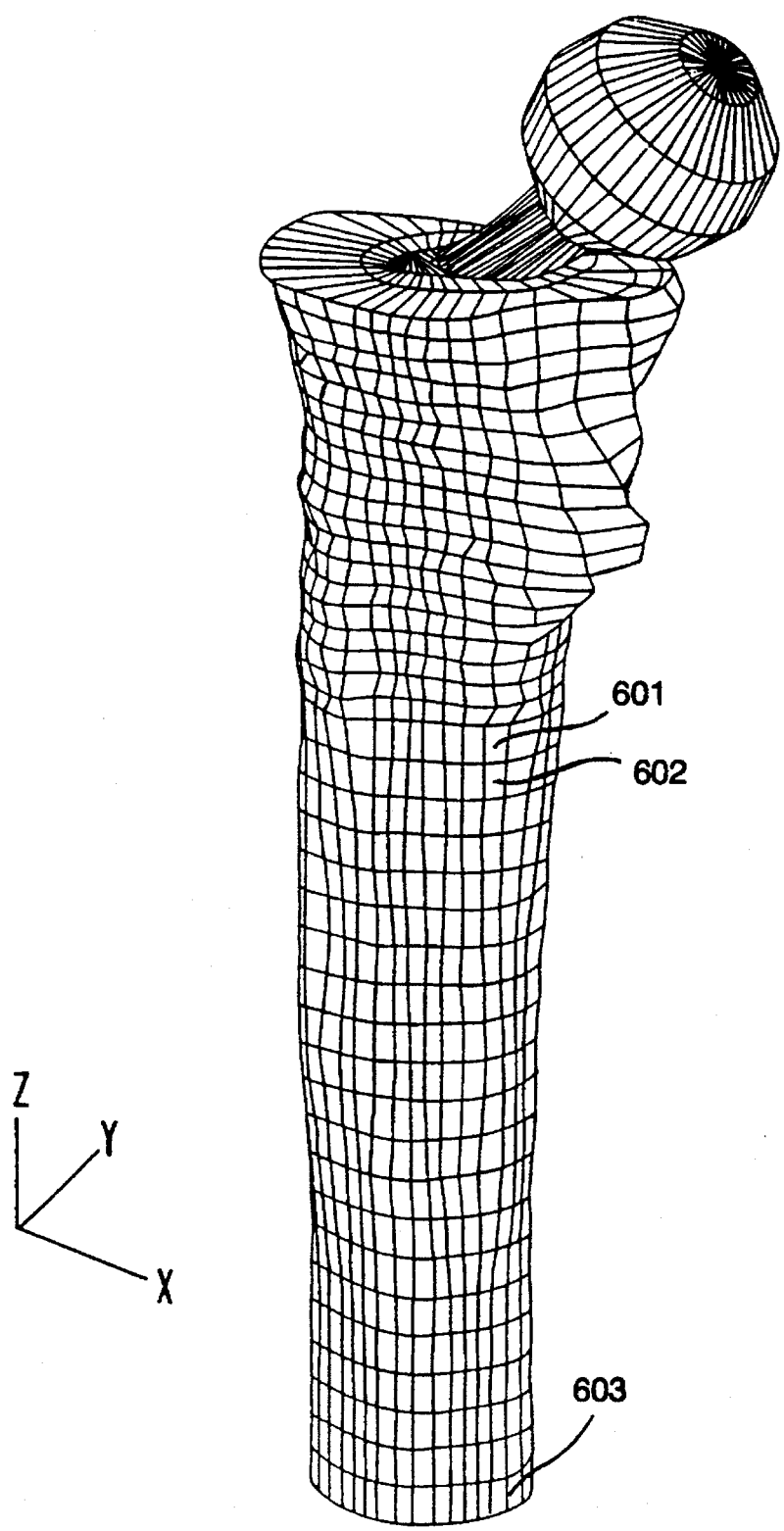
FIG. 6 illustrates a finite element model of a prosthetic hip.

Thus, the finite element model is generated by dividing the geometric model of the object into a plurality of elements and then defining nodes at the boundaries of the elements. An exemplary finite element model for a prosthetic hip is shown in FIG. 6. A variety of element shapes may be used in the finite element model of the object. The number and types of elements selected are generally based on the type of field and the geometry of the object. The various finite element software packages identified above generally include libraries of elements and element clusters to enable modeling of areas having particular geometries with a user-specified degree of accuracy. Thus, an element having an element size of a predetermined value or an element cluster of variable elements having a cluster size of the predetermined value may be utilized. If element clusters are utilized, the cluster may be repeated throughout the finite element model. A cluster may include elements which have different shapes. For example, if the object to be manufactured will be subject to shear forces, elements having shapes which are best suited for modeling shear forces may be utilized and oriented as appropriate. When these elements are grouped together, they may define a cluster which may be repeated, for example, in areas having similar geometries and/or which are applied with similar forces. In addition, different size elements may be used to model object portions of critical tolerance. So-called super-elements may be used where tolerance is not critical. Since the methodology of the invention is typically an iterative process as will be discussed below, if, for example, it is determined in a first iteration that there are one or more portions of the object where the nodal values do not change much, for computational purposes, a second later iteration may generate a finite element model of the object which includes one or more super-elements in these areas in order to simplify subsequent calculations.

The finite element model is completed by specifying the values and/or directions of the above-described fields $\{f\}$ and potentials $\{x\}$ at the nodes of the discretized object. In addition, any appropriate boundary conditions are imposed.

At step 24, the finite element software package is programmed to solve for the material property matrix $[k]$ using the relationship $\{f\}=[k]\{x\}$. That is, $$[k]\{x\}=\{f\}$$

$$[k]\{x\}\{x\}^{-1}=\{x\}^{-1}\{f\}$$

$$[k]=\{x\}^{-1}\{f\}$$

Since the field $\{f\}$ and the potential $\{x\}$ have been defined at step 21, the material property matrix $[k]$ may be calculated. When $\{f\}$ is the mechanical force field and $\{x\}$ is the displacement, $[k]$ is the stiffness matrix. When $\{f\}$ is the thermal flux field and $\{x\}$ is the temperature, $[k]$ is the thermal conductivity. When $\{f\}$ is the magnetic field and $\{x\}$ is the magnetic vector potential, $[k]$ is the magnetic reluctivity. When $\{f\}$ is an electric current field and $\{x\}$ is the voltage, $[k]$ is electrical conductivity, The calculation of the matrix $[k]$ at step 24 when the fields and potentials have been defined as described at steps 21 determines the optimum or near-optimum material property matrix for permitting a manufacturer to manufacture an object having desired responses for a specific application, i.e., for a specific application of forces.

At step 25, the finite element software package is used to extract the material property coefficients for each of the elements in the finite element model from the material property matrix $[k]$. Specifically, the material property matrix $[k]$ which is calculated at step 24 is the global or assembled material property matrix $[k]$. As previously discussed, the material property coefficients for a particular element of the finite element model may be extracted from such a global or assembled matrix using a boolean locating function or some other locating function. For example, with reference to FIG. 6, the material property coefficients for element 601 are extracted, followed by the material property coefficients for element 602, etc. This procedure is repeated for each element in the model in order to generate a data sequence representing the material properties of the prosthetic hip at small volume increments.

Figure 7A:
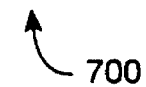
FIGS. 7A and 7B illustrate material properties data bases.
Figure 7B:

At step 26, the extracted material property coefficients are compared with known material property coefficients in a material property data base or data bases. FIG. 7A illustrates one organization of a material property data base 700. Material property data base 700 characterizes a plurality of materials M1-1, M1-2, . . ., M1-n by the values of stiffness properties such as Young's modulus (E) and Poisson's ratio ($\sigma$). For example, material M1-1 may be aluminum having a Young's modulus of $7.2 \times 10^{10}$ Pa and a Poisson's ratio of 0.32. Material M1-2 may be aluminum having a Young's modulus of $6.9 \times 10^{10}$ Pa and a Poisson's ratio of 0.35. Material M1-n may be cast iron having a Young's modulus of $8.8 \times 10^{10}$ Pa and a Poisson's ratio of 0.30. Of course, the invention is not limited to these specific materials. Respectively associated with each of these materials M1-1, M1-2, . . ., M1-n are a manufacturing process and the specific parameters of that process (such as temperature, pressure, etc.) which will produce the material with the corresponding stiffness properties. Similarly, as shown with reference to FIG. 7B, a material property data base 701 may characterize a plurality of materials M2-1, M2-2, . . ., M2-n by the values of electrical conductivity ($\sigma'$). Again, respectively associated with each of these materials M2-1, . . ., M2-n are a manufacturing process and the specific parameters of that process which will produce the material with the corresponding electrical conductivity. Similar material data bases may be used to characterize materials by their thermal conductivity or magnetic reluctivity and to identify the manufacturing method and manufacturing parameters associated with each material.

Thus, the material property data bases are archives of material property coefficients with their corresponding manufacturing process and manufacturing-process control parameters. Such data bases are created and maintained by industrial manufacturers, government agencies, and research institutes. For example, when a material such as a metal, a plastic, or a composite is created using a particular manufacturing process, its properties may be determined through standard testing methods such as ASTM testing methods. When these properties have been determined, the set of manufacturing parameters such as temperature, pressure, etc. which was used to create the material having these properties is correlated to the material in order that the material may be reproduced in the future.

The comparison at step 26 between the extracted material property coefficients and the material properties data base is used to determine which material in the data base has material properties which match or most closely match the properties corresponding to the extracted material property coefficients. Thus, referring to FIG. 6, the comparison will result in the identification of a first set of manufacturing parameters which will produce the portion of the prosthetic hip corresponding to element 601 with the desired stiffness properties; the identification of a second set of manufacturing parameters which will produce the portion of the prosthetic hip corresponding to element 602; etc. The above-described comparisons may be carried out, for example, using a knowledge base having a fact base for storing the extracted material property coefficient data for each of the elements (e.g., elements 601, 602, etc. of FIG. 6) and the material property data from the material data base, and a rule base containing rules for comparing and matching the extracted material property data for each of the elements and the material property data from the material data base. The level of matching (e.g., a perfect match, a close match) is application specific and is related, inter alia, to how much tolerance is permitted. If the object to be manufactured is a critical component, a very close or perfect match is desirable. If the object to be manufactured is a non-critical component, the matching criteria may be relaxed. Other criteria such as cost and the available manufacturing equipment may also determine the level of matching. Thus, by performing step 26, the sets of manufacturing-process control parameters for each and every portion of object are determined.

At step 27, the determined sets of manufacturing-process control parameters are ordered or sequenced to define the manufacturing-process controls which are necessary to manufacture the object. The manufacturing control parameters may be used to implement numerical control of the manufacturing equipment used to manufacture the object. Numerical control refers to the use of coded numerical information in the automatic control of manufacturing equipment. For machine tools, this might refer to the motion of the cutting tool or the movement of the part being formed against a rotating tool. The process of laying composite material to form lightweight alternatives to machined metal parts may also be implemented using numerical control. The necessary geometry and motion statements for manufacturing the object may then be programmed using a general purpose numerical control language to develop manufacturing control data. One such language is APT-AC Numerical Control Processor Program (available from IBM Corporation, Armonk, N.Y.). The APT-AC processor is a computer application program that accepts as input user-oriented language statements that describe the numerical control operations to be performed. A postprocessor may further process the manufacturing control data to tailor the information to a specific manufacturing process. At step 28, the postprocessed data is supplied to a computerized manufacturing device which uses the supplied data to control the manufacturing of the object. The data supplied to the computerized manufacturing device controls the manufacturing device to synthesize the object, which object has the desired specifically calculated material properties. For example, assume the manufacturing is carried out using a braider for manufacturing a composite material. During the weaving of the composite, by allowing the computer to control the speed of various machine parts, the rightness of the weave is controlled. The tighter the weave, the higher the stiffness (low flexibility). For example, in the ease of the prosthetic hip, regions of both high and low stiffness are required. Using the geometric model and the extracted material property coefficients, the manufacturing process and specifically, the tightness of the weave, can be controlled to provide a region of high stiffness (e.g., the region defined by element 601 in FIG. 6) and a region of low stiffness (e.g., the region defined by element 603 in FIG. 6). By appropriately controlling the manufacturing process in accordance the inventive methodology, a prosthetic hip may be produced which responds to applied loads in a manner which is substantially identical to manner in which the human hip would respond to the same applied load. Such a prosthesis can be developed with specific response characteristics for a particular individual.

The above-described methodology is typically carried out as an iterative process. For example, the results of an initial iteration may generally indicate that a fiber composite manufactured using a braider provides the best match to the extracted material property coefficients in the intended application. Thus, in a second subsequent iteration, the finite element model may be modified to take into account the smallest incremental volume that can be controllably braided using a computer-controlled braider. Preferably, each of the elements in the finite element model corresponds to no less than the smallest incremental volume that can be controllably manufactured using the manufacturing technique by which the object is to be manufactured. For example, for a braiding process using a braider, the smallest volume that can be controllably braided is approximately one cubic millimeter. In other words, it is possible to controllably vary a braid pattern to produce an object having material or constitutive properties which vary on the order of a cubic millimeter. This smallest incremental volume will of course vary in accordance with the manufacturing process or technique selected and may, in addition, be dependent on available manufacturing equipment. Thus, although the smallest incremental volume that can be braided by a state-of-the-art braider is one cubic millimeter, it is not necessarily true that all braiders will be capable of such operation. Accordingly, in such cases, the smallest incremental volume is determined by the capabilities of an available braider. It will be appreciated that as manufacturing techniques improve and smaller incremental volumes can be controllably manufactured, the methodology of the instant invention may be utilized with resized or different shaped elements.

The mathematics of the inventive method are valid for other types of manufacturing processes other than composites such as the manufacturing of metals, plastics, and ceramics. The inventive method is also valid for manufacturing objects based on their desired responses to heat and electric currents. In short, the inventive method can be used for any computer controlled manufacturing process, where precision volumetrically controlled manufacturing is desired.

The method of the present invention is particularly useful when increased efficiency of an object is desired. In traditional manufacturing, the emphasis is on precision manufacturing of an object's geometry, without much, if any, control over the internal structural makeup of this geometry. In accordance with inventive methodology, the material matrix is the unknown and an iterative process may be carded out to optimize the material property matrix while keeping the geometry fixed.

Thus, in accordance with the present invention, the input parameters of any process may be precisely varied to create an object with a precisely defined material property matrix. As manufacturing continues to improve, the above-described methodology is applicable even though the smallest incremental volume that can be controllably manufactured may continue to decrease in size.

Figure 8:
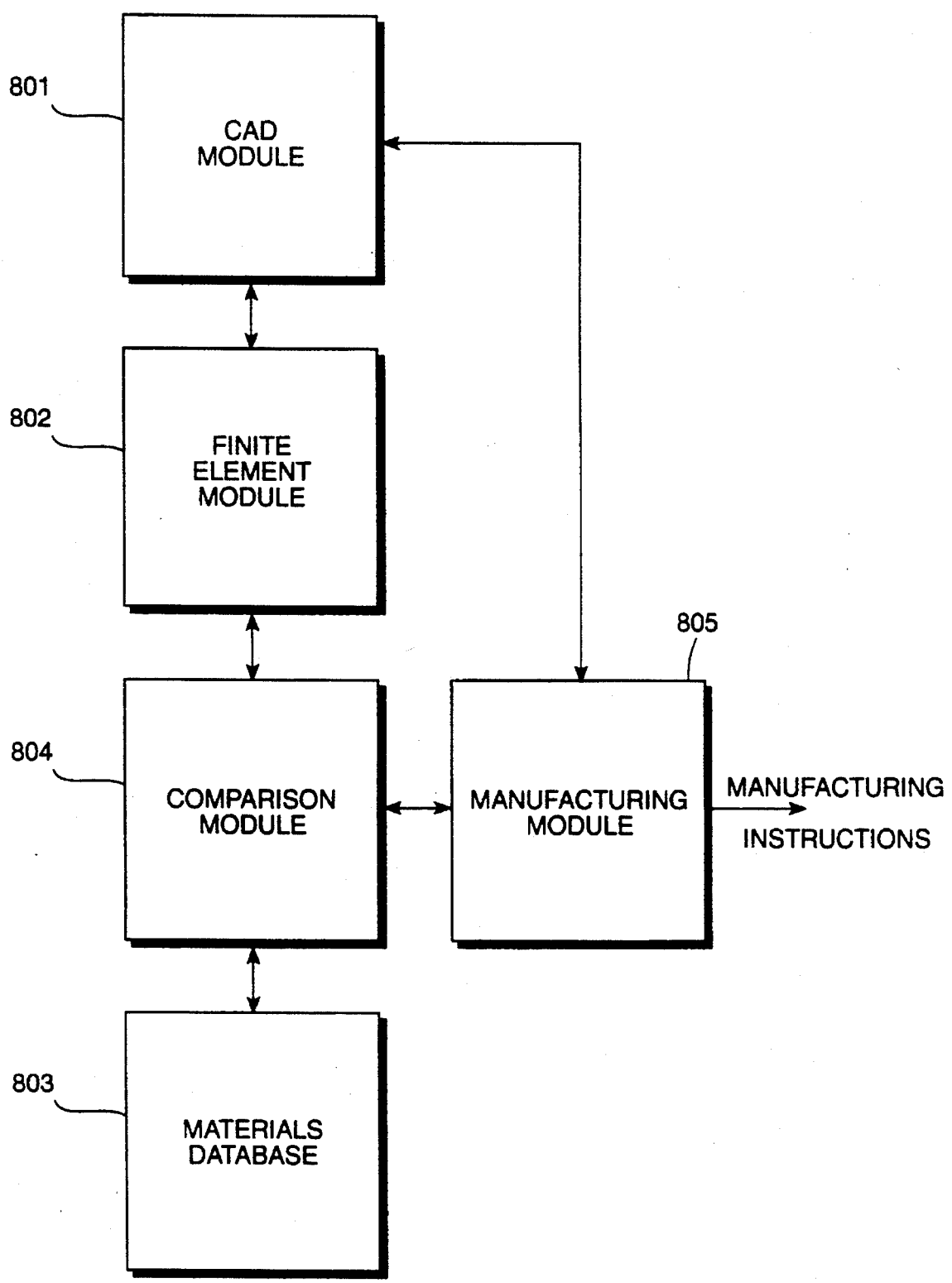
FIG. 8 illustrates functional modules which may be used to implement the present invention.

FIG. 8 illustrates various functional modules which may be used to implement the methodology of the instant invention. A computer-aided-design (CAD) module 801 is a three-dimensional graphics software program for generating an geometrical model definition. Such a geometrical model definition includes coordinate points precisely locating the object design in a three-dimensional coordinate system. This may be provided by a graphics software package using, for example, X, Y, and Z coordinate points and appropriate locating vectors where necessary. The three-dimensional graphics software package utilizes appropriate data structures for derming particular points in the data base of the graphics program. By utilizing algorithms in the graphics program, other points in the object can be defined and generated. The graphics program preferably utilizes appropriate vector and matrix routines whereby an object can be rotated or otherwise moved in computer memory and can be dimensioned whereby the coordinates for any one point are known with respect to other points. As noted above, suitable CAD software packages include I-DEAS (available from SDRC, Inc. of Milford, Ohio), CATIA (available from IBM), and ANVIL-5000 (available from Manufacturing Consulting Services).

A finite element module 802 is used to generate the finite element model of the object from data stored in the graphics program data base. Finite element module 802 is a software package for dividing the object designed using computer-aided-design module 801 into a plurality of elements and expressing one or more unknown field variables in terms of assumed approximating functions within each element. Finite element module 802 is programmed to calculate the optimum material properties for each element as discussed above. Suitable software packages for finite element module 802 include MSC/NASTRAN (available from MacNeal-Schwendler Corporation), ABAQUS (available from Mac-Neal-Schwendler Corporation), and ANSYS (available from Swanson Manufacturing).

A materials data base module 803 is an archive or archives of material property coefficients with their corresponding manufacturing process and manufacturing-process control parameters. The archives thus correlate the properties of materials to the manufacturing process and manufacturing process parameters used to create the materials.

A comparison module 804 compares the material properties determined using finite element module 802 to the material data in material data base module 803 in order to determine (1) which material has material properties which match or most closely match the material properties determined using finite element module 802 and (2) the manufacturing process and manufacturing process parameters associated with this matched material. Comparison module 804 may be implemented, for example, by a knowledge base having a fact base for storing material property data from finite element module 802 and material property data from material data base module 803 and a rule base containing rules for comparing and matching the material property data from finite element module 802 and the material property data from material data base module 803.

A manufacturing module 805 translates and sequences the manufacturing parameters derived from comparison module 804 to provide manufacturing instructions to a manufacturing machine for manufacturing an object in having the geometry defined using computer-aided-design module 801. The manufacturing of the object may be carried out by a machine suitable for the particular material. For example, metals may be manufactured by reproducing surface geometry (surface points in space), composites may be manufactured by controlling weave configuration and fiber choice, and polymers may be manufactured by chemical choice, temperature, and pressure. Computer assistance in manufacturing allows machines to be quickly adjusted to vary the manufacturing process from one object to the next or within various regions of a single object.

Figure 9:
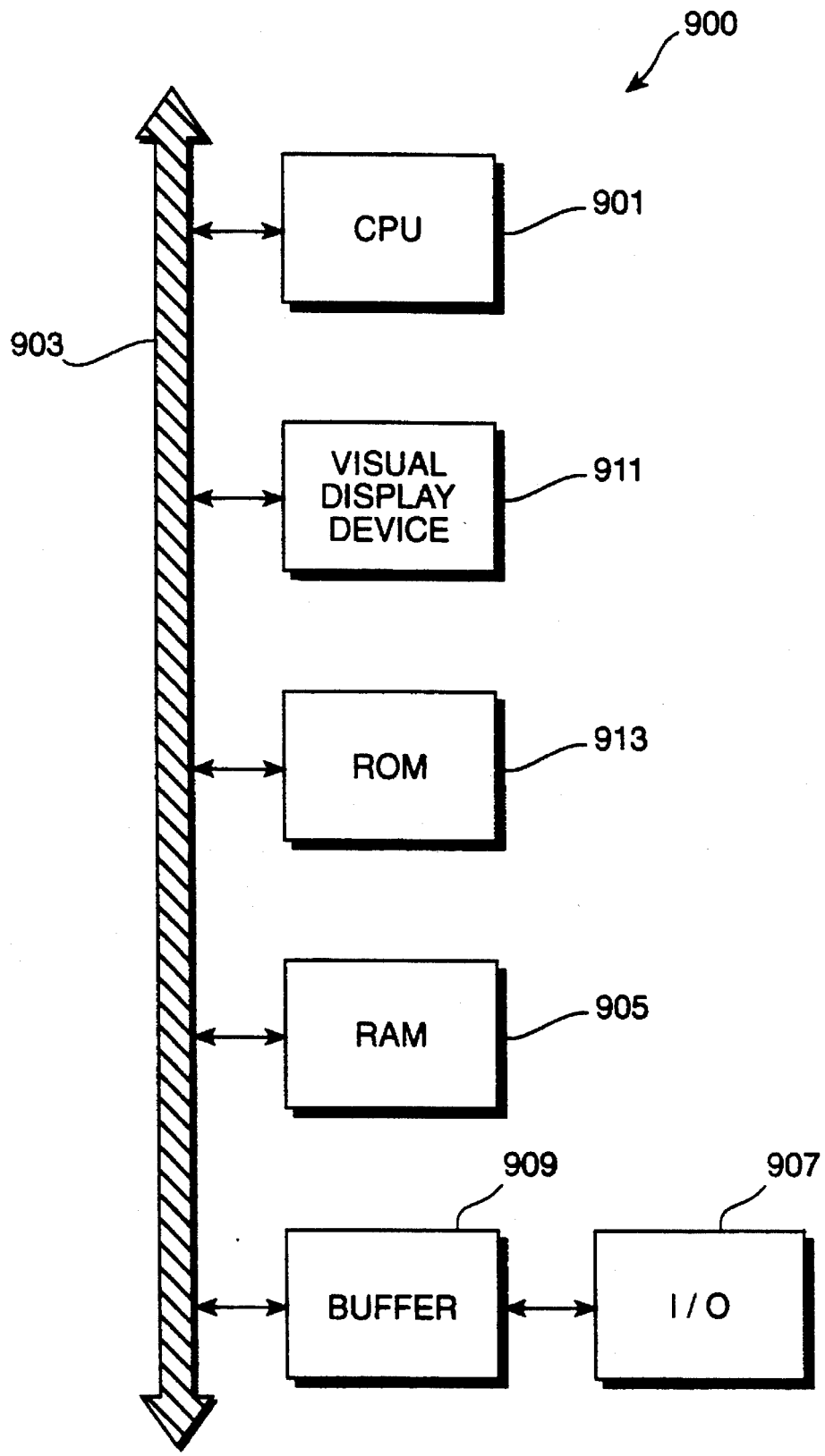
FIG. 9 is a block diagram of an environment which may be used to implement one or more of the functional modules of FIG. 8.

FIG. 9 is a block diagram of the configuration of an environment 900 which may be used to implement the various functional modules described above. Examples of this environment include (but are not limited to) IBM-PC compatible personal computers and UNIX-based workstations such as those available from Sun Microsystems or Silicon Graphics. It should be understood that the environment of the instant invention is not limited to any type or brand of computer, and thus contemplates microcomputers to supercomputers. In addition, while FIG. 9 illustrates the details of a single environment, the modules of FIG. 8 may be implemented on more than one environment. For example, a first environment may be used to implement CAD module 801 while a second different environment may be used to implement finite element module 802. Information may be exchanged between environments using floppy disks or using standard communication packages. Alternatively, a single environment may be used to implement both CAD module 801 and finite element module 802. Environment 900 includes a central processing unit (CPU) 901 such as a RISC-based or an IBM PC-compatible CPU which is plugged into bus 903. One or more of the modules of FIG. 8 are loaded in memory 905 during operation. Input is received via an I/O device 907, after which the input passes through a buffer 909 and then to memory 905 via bus 903. It should be understood that the I/O device can be any standard input device, such as a disk, tape, keyboard, mouse, touch screen, or any compatible or equivalent means for manually or automatically entering information or commands. In order for a user to observe the results as information is entered into the present invention and as progress is made, a preferred embodiment also contemplates the use of a visual display device 911 as an example of an output devices. Other output devices could include printers, magnetic or optical disk, tape, etc. A ROM 913 may store programs for the overall control of environment 900.

Figure 10:
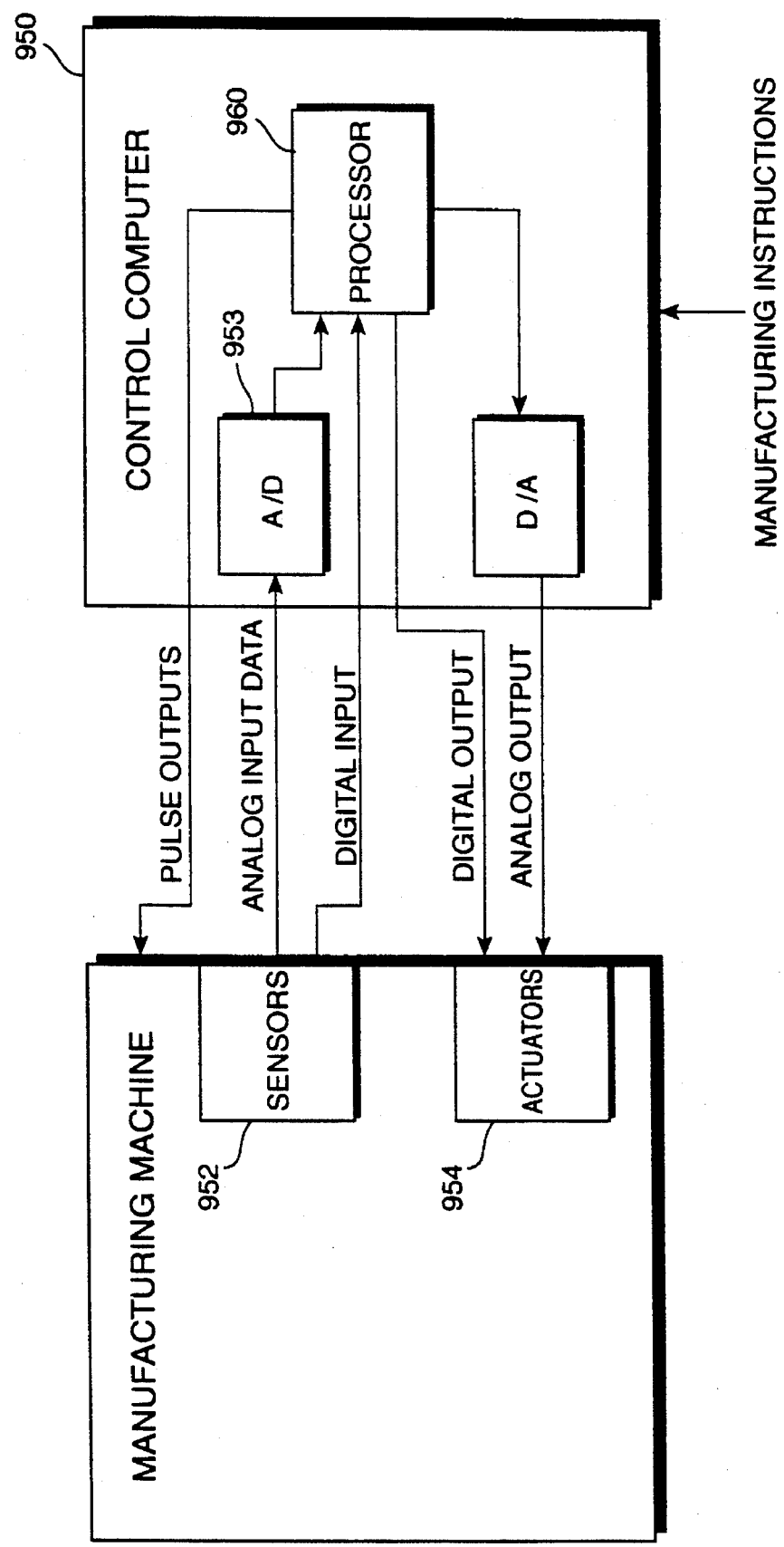
FIG. 10 is a schematic of a control computer for controlling a manufacturing machine.

FIG. 10 is a control computer schematic for a generalized control computer using a control computer 950. The control computer is downloaded with the manufacturing instructions generated by manufacturing module 805 of FIG. 8. Information such as braider bed speed, fiber tension, temperature, pressure, etc. is obtained from sensors 952 of a manufacturing machine in digital format (on/off, open/closed) or analog format (voltage). Analog inputs are converted to a digital representation by analog-to-digital converter 953 of control computer 950. Control computer 950 includes a processor 960 for analyzing the information from sensors 952 and generating signals which are supplied to actuators 954 for adjusting the settings of the manufacturing machine in accordance with the downloaded manufacturing instructions. In addition to analog and digital outputs, pulse outputs may be provided to drive stepping motors, frequently used with machine tools and other equipment. Of course, the specifics of control computer 950 will depend on the manufacturing machine which is utilized. Details of control computers useful in specific manufacturing processes may be found, for example, in the above-identified Bedworth text.

The following examples are provided to illustrate applications of the methodology of the instant invention.

EXAMPLE I

The manufacturing of a composite fiber golf club shaft in accordance with the present invention will be described. In the case of the golf club shaft, the governing equation is $$\{f\}=[k]\{x\}$$

A finite element model of the golf club shaft is created. Golf dub manufacturers maintain data bases which specify the forces {f} a shaft is subjected to (torsion, compression, tension, etc.) for different dub head speeds. These forces are used to define the forces at the nodes of the finite element model.

A golfer generally desires a golf club shaft to respond in a particular way to these various forces. For example, a golf professional generally wants the shafts for a pitching wedge, nine-iron, and eight-iron to have a flex point (i.e., a point of relatively low stiffness) near the club head; the shafts for a seven-iron, a six-iron, and a five-iron to have a flex point near midshaft; the shafts for a four-iron, a three-iron, and a two-iron to have a flex point just above midshaft; and the shaft for a driver to have a flex point just below the grip. In each of these four cases, the shaft thus has a unique set of desired deflections {x}. These desired deflections {x} thus define the displacements at the nodes of the finite element model. Accordingly, four different finite element analyses are carried out.

Since the forces and the displacements of the finite element model have been defined, the global stiffness matrices for each of the four cases may be calculated. Using boolean locating functions, the stiffness coefficients for the individual elements are determined. These determined stiffness coefficients are matched with stiffness coefficients from industrial databases. The manufacturing parameters corresponding to the matched coefficients are appropriately translated and sequenced to generate manufacturing instructions. These manufacturing instructions are then supplied to a composite weaving machine and the braider bed speed and the fiber tension are appropriately controlled to produce the golf shafts. For example, if it is determined that a carbon fiber provides the best match to the determined stiffness coefficients, a carbon fiber is placed on an appropriate weaving machine. As the weaving is performed, the speed of the braider bed and the tension on the fibers is varied in accordance with the generated manufacturing instructions so that certain portions of the golf club shaft will have a tight weave and other portions will have a looser weave. Portions of the shaft having the tighter weave will be stiffer than portions with the loose weave.

EXAMPLE II

The manufacturing of a carbon fiber filled composite hip replacement in accordance with the present invention will be described. In the case of a composite hip replacement, the governing equation is once again $$\{f\}=[k]\{x\}$$

First, a finite element model of the normal bone geometry (both cortical and cancellous layers) is created. The stiffness properties of each layer are then defined. These stiffness properties are a function of Young's modulus and Poisson's ratio. These stiffness properties are used to define the stiffness at the nodes of the finite element model. Next, the loads of walking, rising from a chair, climbing stairs, etc. are defined. These loads are used to define the forces at the nodes of the finite element model. These stiffness properties and loads are known quantities which have been published in numerous journals, e.g., Hodge et al., *Contact Pressures in the Human Hip Joint Measured In Vivo*, Proc. Natl. Acad. Sci. USA, 83 2879–2883 (1986); Fung, *Biomechanics, Mechanical Properties of Human Tissue*, Springer-Verlag, New York (1981).

Since the forces {f} and the stiffness [k] of the finite element model have been defined, the displacements {x} (which are mathematically related to the stress) may be determined. Using boolean locating functions, the resulting matrix data is analyzed to determine the stress at the elements of the finite element model.

Since the stress {x} at the elements of the finite element model has been determined, it may now be treated as a known quantity and represents the ideal stress distribution that it is desired to achieve in the composite hip replacement. Thus, the material stiffness matrix [k] may now be treated as an unknown.

A finite element model is again created, but now includes another layer, namely, the artificial hip embedded in the cancellous bone area. For example, as discussed in St. Ville et al., *"The Anatomy of Midthigh Pain After Total Hip Arthroplasty"*, a finite element analysis may be performed using the fine mesh model of FIG. 6 which includes 5207 nodes and 5040 isoparametric solid elements. Both hexahedronal and pentahedronal elements are used in the mesh of FIG. 6 to ensure accurate shape adherence. The previously calculated displacement data $\{x\}$ defines the displacement at each node of the finite element model.

The loads it is desired to subject the composite hip replacement to are defined. Thus, loads such as walking, one leg stance, etc. are used. The choice of loads depends on the nature of the composite hip replacement being designed. These loads are generally known quantities as noted above, for example, with respect to Hodge et at., "Contact Pressures in the Human Hip Joint Measured In Vivo," *Proc. Natl. Acad. Sci. USA*, 83,.2879–2883 (1986). These loads define the forces $\{f\}$ at the nodes of the finite element model.

Since the displacement $\{x\}$ and forces $\{f\}$ at the nodes of the finite element model have been defined, the global stiffness matrix [k] may be calculated. Using boolean locating functions or other types of locating functions, the stiffness coefficients at each of the nodes are determined. Iterative optimization techniques may be used to calculate the ideal stiffness properties at the elements of the finite element model.

These determined stiffness coefficients are matched with stiffness coefficients from a material property data base. The manufacturing parameters corresponding to the matched coefficients are appropriately translated and sequenced to generate manufacturing instructions. These manufacturing instructions are then supplied to a composite weaving machine and the braider speed and the fiber tension are appropriately controlled to produce the composite hip replacement.

Of course, it should be understood that the present invention contemplates other configurations of modules, and it is not limited to the specific implementation noted above.

Any application, patent, technical document, textbook, or other publication cited herein should be construed to be incorporated by reference as to any subject matter deemed essential to the present disclosure.

While various embodiments of the present invention have been described above, it should be understood that they have been presented by way of example, and not limitation. Thus, the breadth and scope of the present invention should not be limited by any of the above-described exemplary embodiments, but should be defined only in accordance with the following claims and their equivalents.

I claim:

1. A method for manufacturing an object having a potential $\{x\}$ which is generated in response to a field $\{f\}$ applied thereto, the method comprising the steps of:

designing a geometric model of said object;

generating a computerized mathematical model of said object by discretizing said geometric model of said object into a plurality of finite elements and defining nodes at boundaries of said elements, wherein values of the field $\{f\}$ and potential $\{x\}$ are specified at said nodes;

calculating a material property matrix [k] based on the relationship $\{f\}=[k]\{x\}$;

extracting material property coefficients from said material property matrix [k] for each finite element in said computerized mathematical model;

comparing the extracted material property coefficients to material property coefficients for known materials to match the extracted material property coefficients to the material property coefficients for known materials;

determining manufacturing parameters corresponding to the matched material property coefficients; and manufacturing the object in accordance with the determined manufacturing parameters.

2. The method according to claim 1, wherein the step of creating a computerized mathematical model of the object further includes determining the smallest volume increment which can be manufactured using a computer assisted manufacturing method.

3. The method according to claim 1, wherein the field $\{f\}$ is a mechanical force field and the potential $\{x\}$ is a displacement.

4. The method according to claim 1, wherein the field $\{f\}$ is an electric current field and the potential $\{x\}$ is a voltage.

5. The method according to claim 1, wherein the field $\{f\}$ is a magnetic field and the potential $\{x\}$ is a magnetic vector potential.

6. The method according to claim 1, wherein the field $\{f\}$ is a thermal flux field and the potential $\{x\}$ is a temperature.

7. The method according to claim 1, wherein the field $\{f\}$ is a fluid velocity field and the potential $\{x\}$ is a fluid potential.

8. An article of manufacture having response characteristics which are optimized for a particular application and made in accordance with the method of any one of claims 1–7, wherein different portions of the article have different material properties corresponding to the matched material property coefficients for known materials.

9. A computer-implemented method for determining manufacturing parameters for manufacturing an object having a potential $\{x\}$ which is generated in response to a field $\{f\}$ applied thereto, the method comprising the steps of:

creating a geometric model of said object in a computer;

generating a computerized mathematical model of said object by discretizing said geometric model of said object into a plurality of finite elements and defining nodes at boundaries of said elements, wherein values of the field $\{f\}$ and potential $\{x\}$ are specified at said nodes;

calculating a material property matrix [k] based on the relationship $\{f\}=[k]\{x\}$;

extracting material property coefficients from said material property matrix [k] for each finite element in said computerized mathematical model;

comparing the extracted material property coefficients to material property coefficients for known materials to match the extracted material property coefficients to the material property coefficients for known materials;

determining manufacturing parameters corresponding to the matched material property coefficients; and generating machine control instructions for controlling a machine to manufacture the object in accordance with the manufacturing parameters.

10. A computer-implemented method for determining the material properties of an object having a potential $\{x\}$ which is generated in response to field $\{f\}$ applied thereto, the method comprising the steps of:

creating a geometric model of said object in a computer;

generating a computerized mathematical model of said object by discretizing said geometric model of said object into a plurality of finite elements and defining nodes at boundaries of said elements, wherein values of the field $\{f\}$ and potential $\{x\}$ are specified at said nodes;

calculating a material property matrix $[k]$ based on the relationship $\{f\}=[k]\{x\}$;

extracting material property coefficients from said material property matrix $[k]$ for each finite element in said computerized mathematical model; and comparing the extracted material property coefficients to material property coefficients for known materials to match the extracted material property coefficients to the material property coefficients for known materials.

11. A machine for determining the manufacturing parameters of an object having a potential $\{x\}$ which is generated in response to a field $\{f\}$ applied thereto, comprising:

designing means for designing a geometric model of said object;

generating means for generating a computerized mathematical model of said object by discretizing said geometric model of said object into a plurality of finite elements and defining nodes at boundaries of said elements, wherein values of the field $\{f\}$ and the potential $\{x\}$ are specified at said nodes;

calculating means for calculating a material property matrix $[k]$ based on the relationship $\{f\}=[k]\{x\}$;

extracting means for extracting material property coefficients from said material property matrix $[k]$ for each finite element in said computerized mathematical model;

comparing means for comparing the extracted material property coefficients to material property coefficients for known materials to match the extracted material property coefficients to the material property coefficients for known materials; and determining means for determining manufacturing parameters corresponding to the matched material property coefficients.

12. A machine for determining the material properties of an object having a potential $\{x\}$ which is generated in response to a field $\{f\}$ applied thereto, comprising:

designing means for designing a geometric model of said object;

generating means for generating a computerized mathematical model of said object by discretizing said geometric model of said object into a plurality of finite elements and defining nodes at boundaries of said elements, wherein values of the field $\{f\}$ and potential $\{x\}$ are specified at said nodes;

calculating means for calculating a material property matrix $[k]$ based on the relationship $\{f\}=[k]\{x\}$;

extracting means for extracting material property coefficients from said material property matrix $[k]$ for each finite element in said computerized mathematical model; and comparing means for comparing the extracted material property coefficients to material property coefficients for known materials to match the extracted material property coefficients to the material property coefficients for known materials.

13. The article of manufacture according to claim 8, wherein the different material properties are mechanical stiffness properties.

14. The article of manufacture according to claim 8, wherein the different material properties are thermal conductivities.

15. The article of manufacture according to claim 8, wherein the different material properties are magnetic reluctivities.

16. The article of manufacture according to claim 8, wherein the different material properties are electrical conductivities.

17. An article of manufacture made in accordance with the method of claim 1, wherein the article is selected from the group consisting of an automobile part, an aircraft part, a prosthetic implant, a golf club shaft, a tennis racket, a bicycle frame, and a fishing pole, and wherein different portions of the article have different material properties corresponding to the matched extracted material property coefficients for known materials.

18. A human prosthesis manufactured in accordance with the method of claim 1, wherein the human prosthesis comprises a non-uniform mechanical stiffness throughout causing a different displacement under loading.

19. A golf club manufactured in accordance with the method of claim 1, wherein the golf club comprises a shaft having a plurality of adjacent regions each having a different mechanical stiffness property which provides a different displacement under loading.

20. A method for manufacturing an object for which a defined field $\{f\}$ generates a potential $\{x\}$ in response thereto, the method comprising the steps of:

(1) generating a computerized mathematical model of the object by discretizing a geometric model of the object into a plurality of finite elements and defining nodes at boundaries of each of the finite elements;

(2) specifying values of the field $\{f\}$ and the potential $\{x\}$ for each of the nodes;

(3) calculating a material property matrix $[k]$ based on the relationship $\{f\}=[k]\{x\}$, wherein the material property matrix $[k]$ comprises a plurality of values each corresponding to one or more material property coefficients;

(4) comparing each of the plurality of values in the material property matrix $[k]$ to a known material property and, responsive to a match, selecting a corresponding manufacturing process parameter; and (5) controlling a manufacturing machine in accordance with the selected manufacturing process parameters.

21. The method of claim 20, wherein step (5) comprises the step of controlling the manufacturing machine to control the stiffness properties of the object along an axis of manufacture.

22. An article manufactured in accordance with the method of claim 21, wherein the article comprises a plurality of regions each having a different mechanical stiffness along the axis of manufacture.

23. An article of manufacture comprising a plurality of adjacent fiber composite braided regions each having a different mechanical stiffness property which causes a different regional displacement according to a stress load placed on that region when the material article is used, wherein each different stiffness mechanical property is determined by a manufacturing process which calculates each stiffness based on a specified potential at nodes of a geometric model of the article of manufacture.

24. A computer programmed with machine control instructions for controlling a manufacturing machine to manufacture an article in accordance with a plurality of manufacturing parameters, wherein the machine control instructions are generated on the basis of a process which optimizes the manufacturing parameters for a particular application in response to a plurality of desired displacement values for different regions of the article, and wherein the machine control instructions control settings of the manufacturing machine on the basis of sensor data received from the machine and the plurality of manufacturing parameters to manufacture the article with a plurality of different regions each having a different mechanical stiffness property which provides a different displacement under loading.

* * * * *